United States Patent [19]

Slocum

[11] Patent Number: Plant 5,798

[45] Date of Patent: Nov. 4, 1986

[54] LOTUS PLANT CV MAGGIE BELLE SLOCUM

[76] Inventor: Perry D. Slocum, 191 Leatherman Gap Rd., Franklin, N.C. 28734

[21] Appl. No.: 785,839

[22] Filed: Oct. 9, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A lotus plant having rose pink flowers with rolled petal edges, borne well above the leaves.

4 Drawing Figures

The present invention relates to a new and distinct variety of lotus plant named Maggie Belle Slocum of the decorative class which was originated by Perry D. Slocum, by crossing a *Nelumbo nucifera,* variety: *shirokunshi* with a *Nelumbo nucifera,* variety: *rubrum.*

The primary objective of this breeding was to produce a new and improved lotus variety having a colorful magenta rose pink flower which was hardy with the flowers extending substantially above the leaves. This objective was achieved along with other desirable improvements as evidenced by the unique combination of characteristics which are outstanding in the new variety and which distinguish it from all other lotus varieties by its:

(1) flowers of substantially rose pink;
(2) large flowers; and
(3) flower petals curled (rolled).

Asexual reproduction of the new variety which was performed at Franklin, N.C., by tuber division shows that the foregoing characteristics and distinctions come true to form and are established and transmitted through succeeding propagations.

The accompanying photographs show typical specimens of the leaf, stem, bud and flowers of the new lotus variety in different stages of development and as depicted in color as nearly true as is reasonably possible to make the same in color photographs of this character.

The following is a detailed description of the new variety, with color terminology in accordane with *Exotica,* 8th Edition, published by Roehrs Company, Inc., of New Jersey, Horticultural Color Guide:

Parentage: Seedling.

*Seed parent.—Nelumbo nucifera,* variety: *shirokunshi.*

*Pollen parent.—Nelumbo nucifera,* variety: *rubrum.*

Classification: Decorative.

Height: leaves are approximately 4 to 5 feet above water with 16–24 inch diameters with flowers approximately 10–11 inches in diameter and top of flower approximately 12 inches above leaves.

Location where grown and observed: Outdoors in water pools in Franklin, N.C. from approximately June 20 to September 1.

Cold resistance: Hardy perennial.

Blooming period: In Franklin, N.C. climatic area, blooming begins in June and continues to September.

SEED POD

Seed pod is (non-distinctive) similar to other lotus seed pods.

FLOWER

Figure 2:
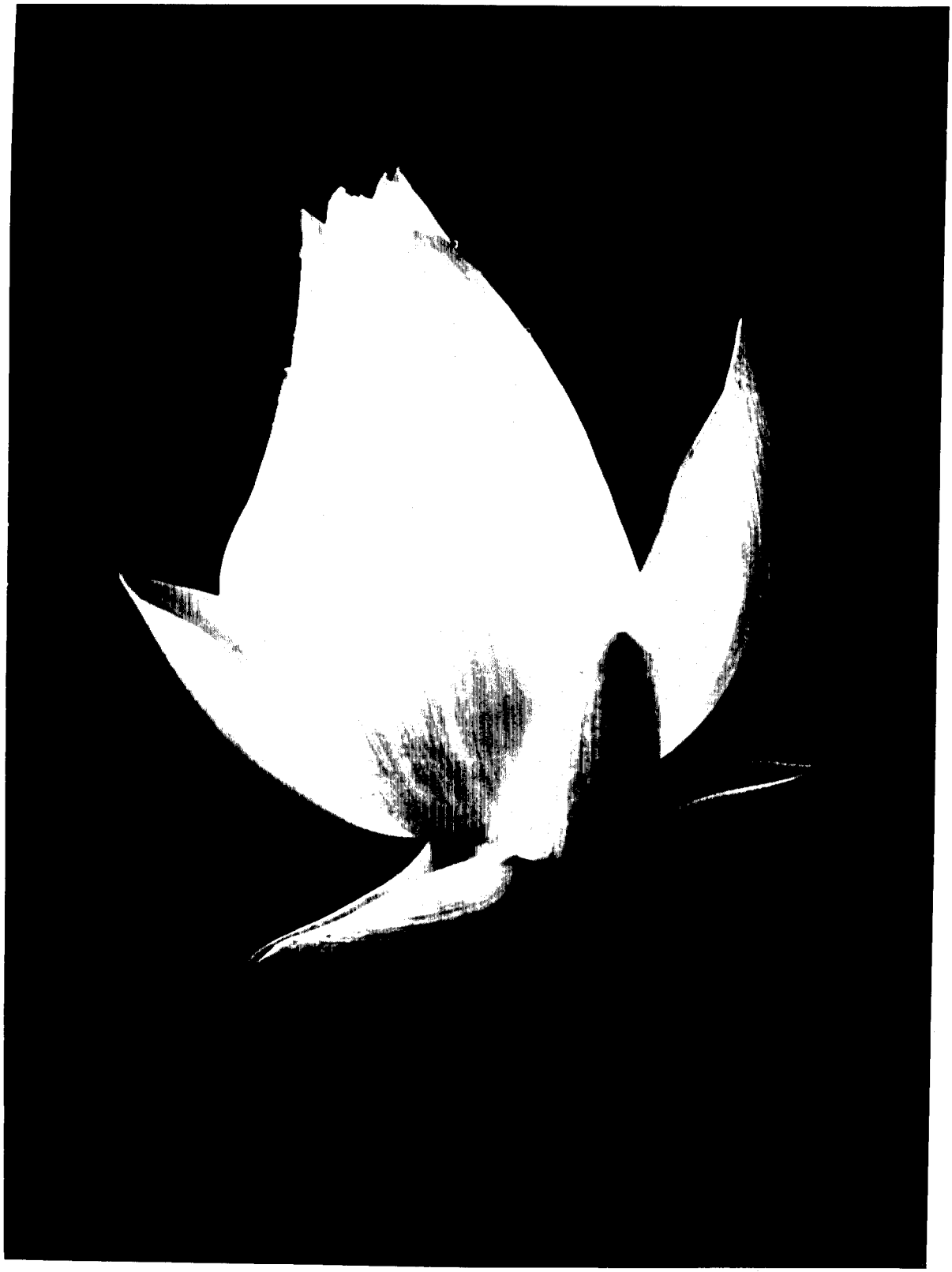

Bud: Color as shown in FIG. 2, upper bud petals have #38 rose petals. Lower bud petals are #73 grass green with #37 rose pink veins with a peduncle of #70 ivy green.

Figure 3:
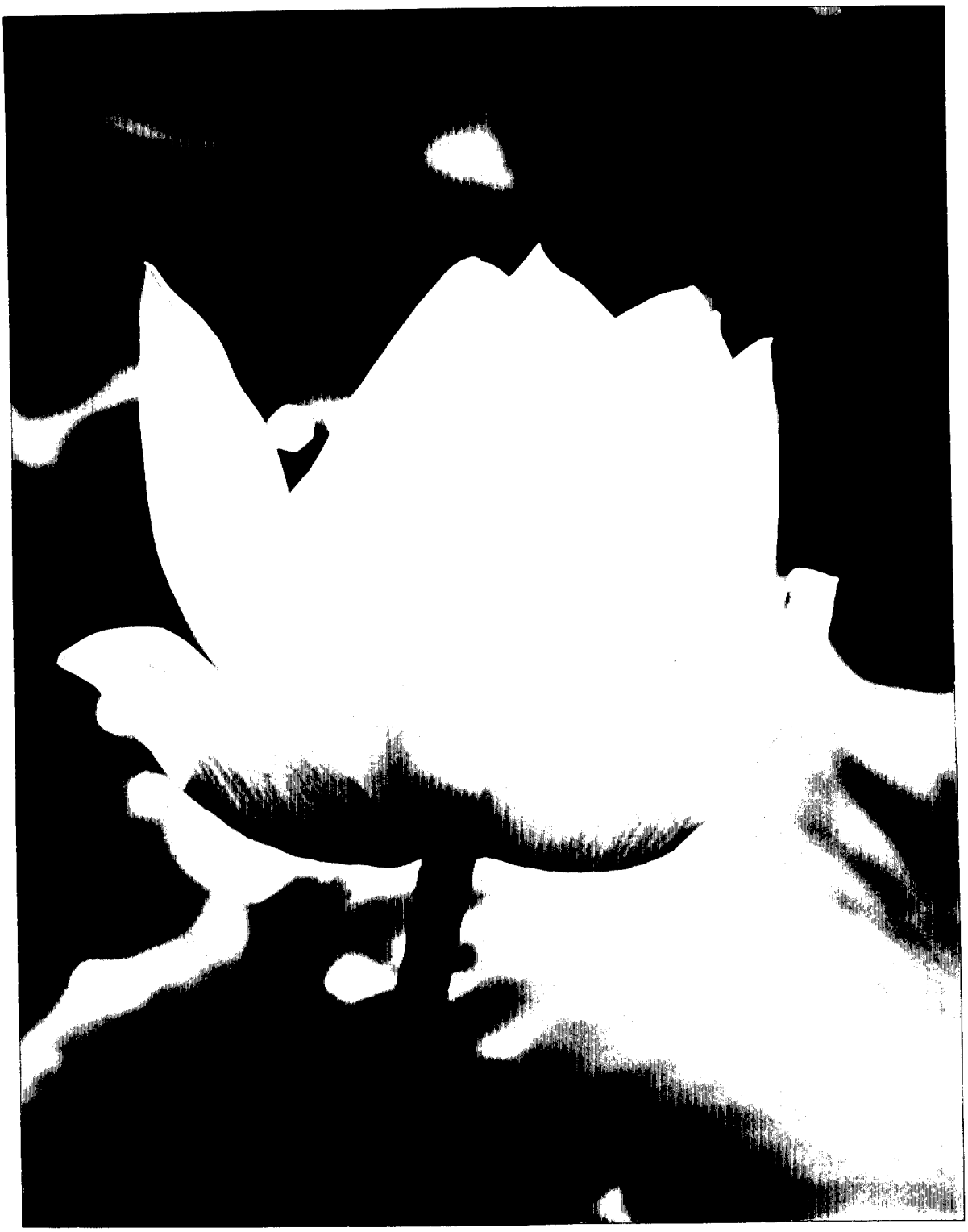

*When petals further divide* (FIG. 3).—Uppermost petals are #38 rose. Lower petals approximate #37 rose pink with #79 citron.

Bloom:

*Size.*—10 to 11 inches in diameter.

*Stem.*—Stiff, strong #73 grass green in color.

Figure 4:
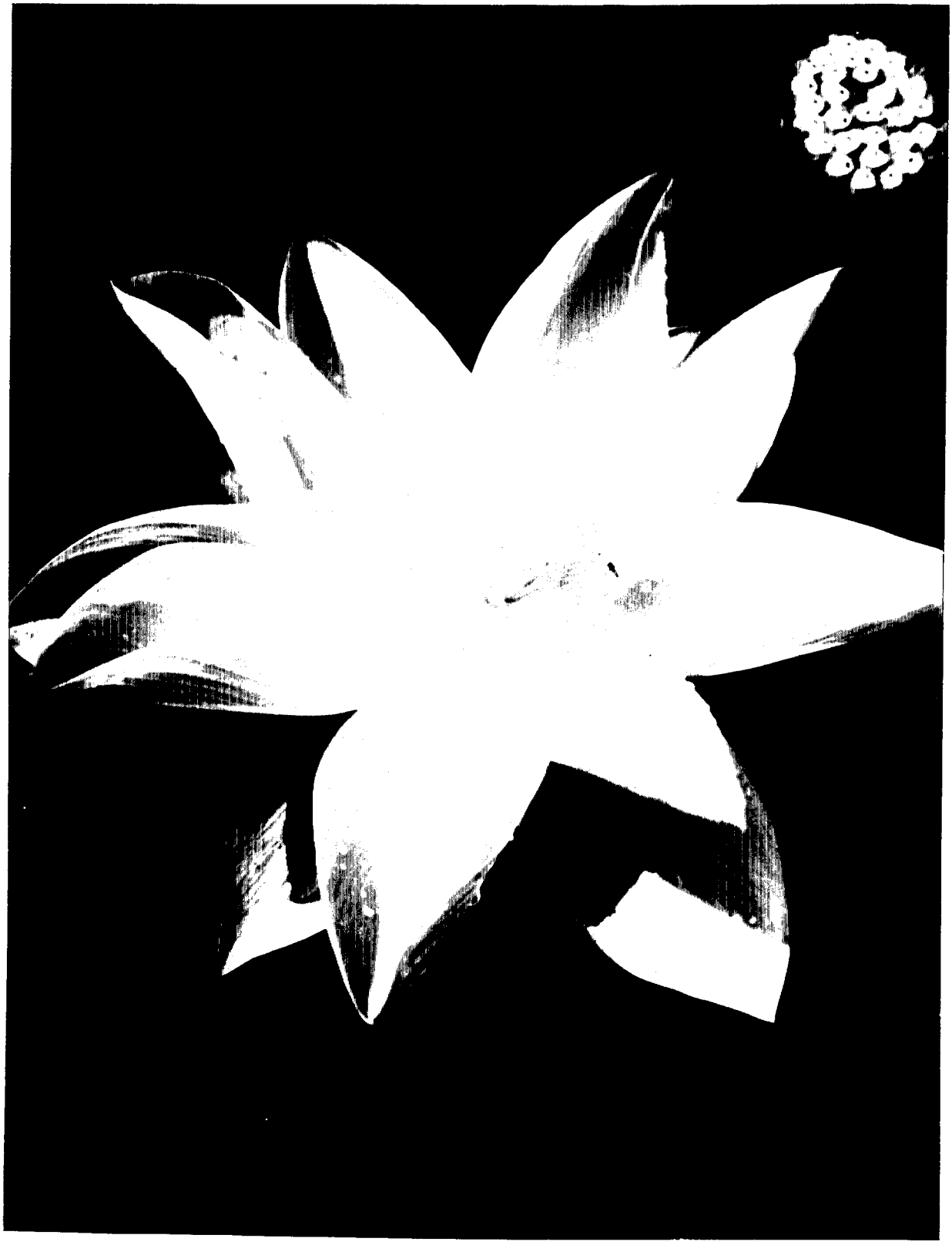

*Form.*—First day flowers are cup shaped, second and third days flowers are fully opened (FIG. 4).

*Petalage.*—16 to 18.

*Color.*—Center of flower — Center of pistils #4 buttercup yellow at the pistil edge #69 bottle green with some blue with anthers between #3 canary yellow and #4 buttercup yellow and stamens #4 buttercup yellow. Petals approximate #38 rose with darker than #38 rose tips.

*Petals.*—Texture — smooth.

*Fragrance.*—Very fragrant, lotus fragrance.

PLANT

Form: All branching of the plant is done under water.

Growth: Medium to large leaves about 4 to 5 feet above water.

Figure 1:
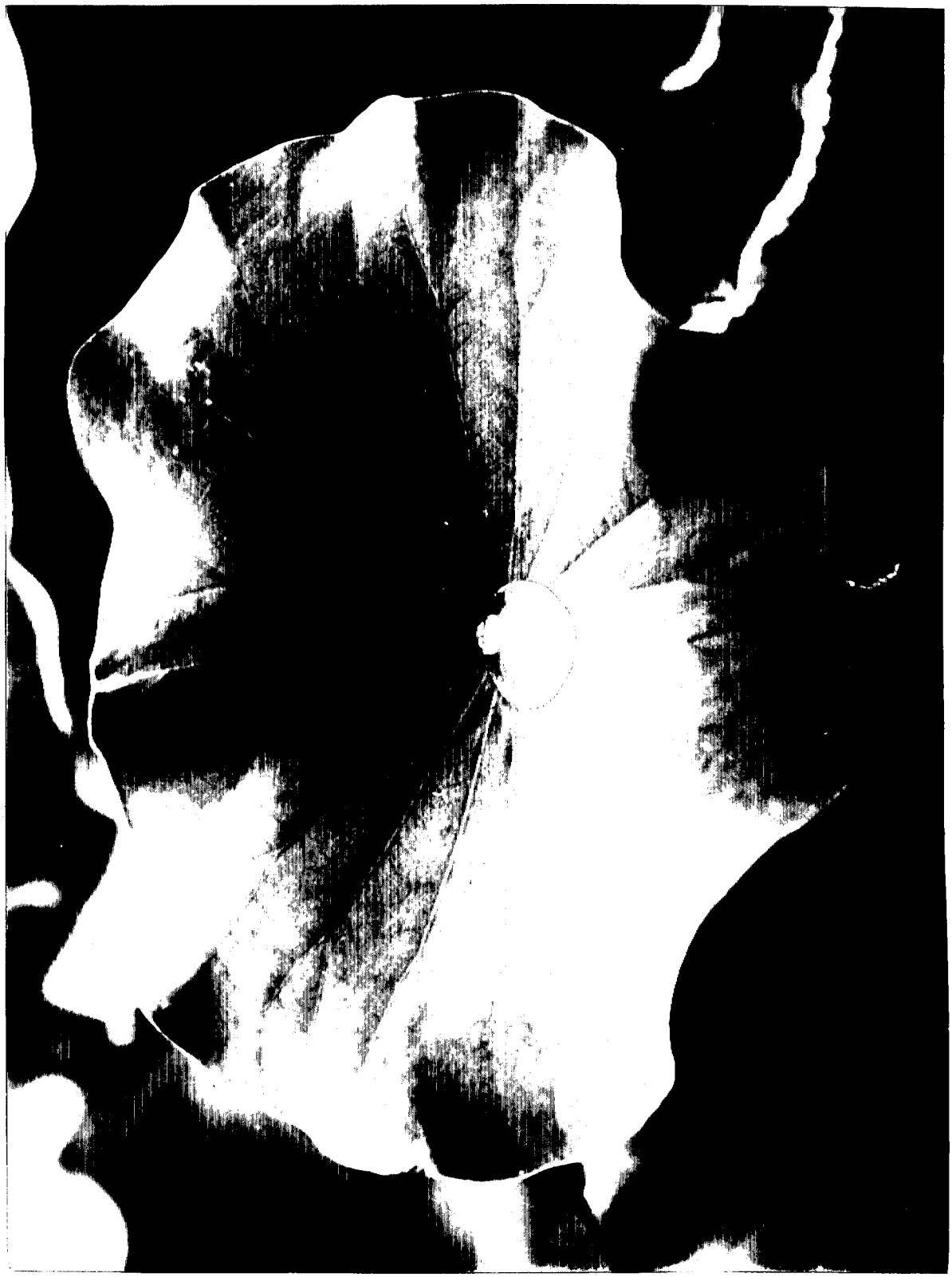

Foliage:

*Size.*—16–24 inch leaf diameter leaves (FIG. 1).

*Quantity.*—Plentiful.

*Color.*—#65 Turquoise with slightly blue veins.

*Texture.—Smooth.*

I claim:

1. A new and distinct variety of lotus plant substantially as herein shown and described.

* * * * *